United States Patent
Venkateswaran et al.

(10) Patent No.: US 9,228,240 B2
(45) Date of Patent: Jan. 5, 2016

(54) METHODS FOR DETECTING AND QUANTIFYING VIABLE BACTERIAL ENDO-SPORES

(75) Inventors: Kasthuri J. Venkateswaran, Azusa, CA (US); Christina N. Stam, Pasadena, CA (US); Ronald D. Smiley, Jefferson, AR (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 53 days.

(21) Appl. No.: 13/152,213

(22) Filed: Jun. 2, 2011

(65) Prior Publication Data

US 2011/0318750 A1 Dec. 29, 2011

Related U.S. Application Data

(60) Provisional application No. 61/351,238, filed on Jun. 3, 2010, provisional application No. 61/441,820, filed on Feb. 11, 2011.

(51) Int. Cl.
C12Q 1/68 (2006.01)

(52) U.S. Cl.
CPC .............. *C12Q 1/689* (2013.01); *C12Q 1/6848* (2013.01)

(58) Field of Classification Search
None
See application file for complete search history.

(56) References Cited

U.S. PATENT DOCUMENTS

| | | | |
|---|---|---|---|
| 4,469,863 A | 9/1984 | Ts'o et al. | |
| 5,034,506 A | 7/1991 | Summerton et al. | |
| 5,216,141 A | 6/1993 | Benner | |
| 5,235,033 A | 8/1993 | Summerton et al. | |
| 5,386,023 A | 1/1995 | Sanghvi et al. | |
| 5,510,270 A | 4/1996 | Fodor et al. | |
| 5,539,083 A | 7/1996 | Cook et al. | |
| 5,556,752 A | 9/1996 | Lockhart et al. | |
| 5,578,832 A | 11/1996 | Trulson et al. | |
| 5,602,240 A | 2/1997 | De Mesmaeker et al. | |
| 5,637,684 A | 6/1997 | Cook et al. | |
| 5,644,048 A | 7/1997 | Yau | |
| 6,449,562 B1 | 9/2002 | Chandler et al. | |
| 6,524,793 B1 | 2/2003 | Chandler et al. | |
| 8,021,848 B2 * | 9/2011 | Straus | 435/7.1 |
| 8,771,940 B2 | 7/2014 | Andersen et al. | |
| 2011/0053790 A1 * | 3/2011 | Yoshida et al. | 506/9 |

FOREIGN PATENT DOCUMENTS

WO 2010/151842 12/2010

OTHER PUBLICATIONS

Nocker et al. (Comparison of propidium monoazide with ethidium monoazide for differentiation of live vs. dead bacteria by selective removal of DNA from dead cells, Journal of Microbiological Methods, 67:310-320, 2006.*
Riedy et al., Use of a Photolabeling Technique to Identify Nonviable Cells in Fixed Homologous or Heterologous Cell Populations, Cytometry, 12:133-139, 1991.*
Nicholson et al. (Resistance of Bacillus Endospores to Extreme Terrestrial and Extraterrestrial Environments, Microbiology and Molecular Biology Reviews, p. 548-572, Sep. 2000.*
Bacterial Endospore, attached, Oct. 23, 2008.*
Henriques et al. (Structure and Assembly of the Bacterial Endospore Coat, Methods, 20:95-110, 2000).*
Rawsthorne et al., PCR-Based Method Using Propidium Monoazide to Distinguish Viable from Nonviable Bacillus subtilis Spores, Applied and Environmental Microbiology, May 2009, p. 2936-2939.*
Liu et al., Formation and Composition of the Bacillus anthracis Endospore, Journal of Bacteriology, Jan. 2004, p. 164-178.*
Laflamme et al. (Assessment of bacterial endospore viability with fluorescent dyes, Journal of Applied Microbiology 2004, 96, 684-692).*
Kelly et al. (Use of the direct epifluorescent filter technique for the enumeration of bacterial spores, Journal of Applied Bacteriology 1987,63, 545-550).*
Yung (Detection of Aerobic Bacterial Endospores: From Air Sampling, Sterilization Validation to Astrobiology, dissertation, attached, available May 9, 2008).*
Kroll (The Direct Epifluorescent Filter Technique (DEFT), in Methods in Molecular Biology, vol. 46: Diagnostic Bacteriology Protocols, Ch. 2, May 23, 1995).*
Sigma (Ethidium Bromide Product Sheet, attached, Apr. 29, 1999).*
Helen Rawsthorne et al., "PCR-based method using propidium monoazide to distinguish viable from nonviable Bacillus subtilis spores," Applied and Environmental Microbiology 75 (2009): pp. 2936-2939.
Amann, R.I., Krumholz, L., and Stahl, D.A. (1990) Fluorescent-Oligonucleotide Probing of Whole Cells for Determinative, Phylogenetic, and Environmental-Studies in Microbiology. J. Bacteriol., 172, 762-770.
La Duc, M.T., Dekas, A.E., Osman, S., Moissl, C., Newcombe, D., and Venkateswaran, K. (2007) Isolation and characterization of bacteria capable of tolerating the extreme conditions of clean-room environments. Appl. Environ. Microbiol., 73, 2600-2611.
La Duc, M.T., Osman, S., and Venkateswaran, K. (2009) Comparative analysis of methods for the purification of DNA from low-biomass samples based on total yield and conserved microbial diversity. J. Rapid Meth. Auto. Microbiol., 17, 350-368.
Suzuki, M.T., Taylor, L.T., and DeLong, E.F. (2000) Quantitative analysis of small-subunit rRNA genes in mixed microbial populations via 5'-nuclease assays. App. Environ. Microbiol., 66, 11, 4605-4614.
Newcombe, D. A., A. C. Schuerger, J. N. Benardini, D. Dickinson, R. Tanner, and K. Venkateswaran. 2005. Survival of spacecraft-associated microorganisms under simulated martian UV irradiation. Appl. Environ. Microbiol. 71:8147-8156.

(Continued)

*Primary Examiner* — Stephanie K Mummert
*Assistant Examiner* — Aaron Priest
(74) *Attorney, Agent, or Firm* — Steinfl & Bruno LLP

(57) ABSTRACT

Methods and systems for detecting viable bacterial endospores in a sample and related methods to quantify viable bacterial endospores in a sample.

14 Claims, 7 Drawing Sheets

(56) References Cited

OTHER PUBLICATIONS

Lee, J.L., et al. (2009) A comparative study of the ability of EMA and PMA to distinguish viable from heat killed mixed bacterial flora from fish fillets. J. of Microbiological Methods, 26, pp. 93-96.

Bae, S., et al. (2009) Discrimination of Viable and Dead Fecal Bacteroidales Bacteria by Quantitative PCR with Propidium Monoazide. Applied and Environmental Microbiology, vol. 75, No. 9, pp. 2940-2944.

Cooper, M., et al. "Assessing the cleanliness of surfaces: Innovative molecular approaches vs. standard spore assays." Appl Environ Microbiol (Jun. 7, 2011).

Sambrook, J. et al. "Molecular Cloning: A Laboratory Manual" Third Edition. pp. A1.16, A1.22 and A1.28. (2001).

"Wikibooks: Principles of Biochemistry/Cell Metabolism I: DNA replication". Retrieved on Aug. 6, 2013.

Barnes, W. "PCT Amplification of up to 35-kb DNA with high fidelity and high yield from a bacteriophage templates" in Proc. Natl Acad Sci. USA vol .91, pp. 2216-2220 1994 (Mar. 1994).

Suzuki, T. et al "Mechanist studies on depurination and apurinic site chain breakage in oligodeoxyribonucleotides" Nucleic Acids Research vol. 22, No. 23 4997-5003 (1994).

Yan, L et al "Fractal aggregation of DNA after thermal denaturation" Chaos, Solitons and Fractals 20 877-881 (2004).

H.K. Nogva, et al., "Ethidium Monoazide for DNA-Based Differentiation of Viable and Dead Bacteria by 5'-Nuclease PCR", BioTechniques, 2003, 34: 804-813.

R. Anderson, et al., "Stimulating the in situ activity of Geobacter species to remove uranium from the groundwater of a uranium-contaminated aquifer". Applied and Environmental Microbiology (2003) 69 (10):5884-5891.

S. Beaucage, et al., "The Functionalization of Oligonucleotides Via Phosphoramidite Derivatives", Tetrahedron, 49(10):1925-1963 (1993).

A. Blanchard, et al., "High-density oligonucleotide arrays", Biosensors & Bioelectronics, 11 (6):687-690 (1996).

M. Bolli, et al., "Ch. 7: α-Bicyclo-DNA: Synthesis, Characterization, and Pairing Properties of α-DNA-Analogues with Restricted Conformational Flexibility in the Sugar—Phosphate Backbone", ASC Symposium Series 580, *Carbohydrate Modifications in Antisense Research*, pp. 100-117 (1994).

W. Brill, et al., "Synthesis of oligodeoxynucleoside phosphorodithio-ates via thioamidites", J. Am. Chem. Soc., 111:2321-2322 (1989).

E. Brodie, et al., "Application of a high-density oligonucleotide microarray approach to study bacterial population dynamics during uranium reduction and reoxidation", Applied Environ Microbiol. (2006) 72 (9):6288-6298.

C. Carlsson, et al., "Screening for genetic mutations", Nature, 380:207 (1996).

M. Chee, et al., "Accessing genetic information with High-Density DNA arrays", Science (1996) 274:610-614.

M. De Hoon, et al., "Open source clustering software", Bioinformatics (2004) 20 (9): 1453-1454.

A. De Mesmaeker, et al., "Ch. 2: Novel Backbone Replacements for Oligonucleotides", ASC Symposium Series 580, *Carbohydrate Modifications in Antisense Research*, pp. 24-39 (1994).

A. De Mesmaeker, et al., "Comparison of Rigid and Flexible Backbones in Antisense Oligonucleotides", Bioorganic & Medicinal Chem. Lett., 4 (3):395-398 (1994).

R. Dempcy, et al., "Synthesis of thymidyl pentamer of deoxyribonucleic guanidine and binding studies with DNA homopolynucleotides", Proc. Natl. Acad. Sci. USA, 92:6097-6101 (1995).

T. DeSantis, et al, "Greengenes, chimera-checked 16S rRNA gene database and workbench compatible with ARB", Applied and Environmental Microbiology (2006) 72 (7):5069-5072.

T. DeSantis, et al., "High-density universal 16S rRNA microarray analysis reveals broader diversity than typical clone library when sampling the environment", Microbial Ecology, 53(3):371-383 (2007).

T. DeSantis, et al., "NAST: a multiple sequence alignment server for comparative analysis of 16S rRNA genes", Nucleic Acids Res. (2006) 34:W394-W399.

M. Egholm, "Peptide nucleic acids (PNA). Oligonucleotide analogs with an achiral peptide backbone", J. Am. Chem. Soc., 114:1895-1897 (1992).

M. Egholm, et al., "PNA hybridizes to complementary oligonucleotides obeying the Watson-Crick hydrogen-bonding rules", Nature 365:566-568 (1993).

J. Evans, et al., "Relaxed neighbor-joining: a fast distance-based phylogenetic tree. Construction Method", J Mol Evol (2006) 62:785-792.

S. Fodor, et al., "Light-directed, spatially addressable parallel chemical synthesis", Science (1991) 251:767-773.

B. Froehler, et al., "Synthesis of DNA via deoxynucleoside H-phosphonate intermediaries", Nucleic Acid Res. 14 (13):5399-5407 (1986).

H. Gao, et al., "Microarray-based analysis of microbial community RNAs by whole-community RNA amplification", Appl. Environ. Microbiol. (2007) 73 (2):563-571.

X. Gao, et al., "Unusual conformation of a 3'-thioformacetal linkage in a DNA duplex", J. Biomolecular NMR, 4: 17-34 (1994).

G. Geiss, et al. "Direct multiplexed measurement of gene expression with color-coded probe pairs", Nature Biotech. 26 (3):317-325, 2008.

S. Goslee, et al., "The ecodist package for dissimilarity-based analysis of ecological data", J Stat Softw (2007) 22 (7):1-19.

M. Hattori, et al., "The Human Intestinal Microbiome: a new frontier of human biology", DNA Research (2009) 16:1-12.

P. Herdewijn, et al., "Ch. 6: Hexopyranosyl-Like Oligonucleotides", ASC Symposium Series 580, *Carbohydrate Modifications in Antisense Research*, 80-99 (1994).

T. Horn, et al., "Oligonucleotides with Alternating Anionic and Cationic Phosphoramidate Linkages: Synthesis and Hybridization of Stereo-uniform Isomers", Tetrahedron Lett., 37 (6):743-746 (1996).

R. Hurt, et al.,"Simultaneous Recovery of RNA and DNA from Soils and Sediments", Appl. Environ. Microbiol. (2001) 67 (10), 4495-4503.

S. Huse, et al., "Exploring Microbial Diversity and Taxonomy Using SSU rRNA Hypervariable Tag Sequencing", Plos Genetics (2008) 4 (11): e10000255. (10 pages).

G. Jenkins, et al., "The Biosynthesis of Carbocyclic Nucleosides", Chem. Soc. Rev., (1995), pp. 169-176.

P. Jung, et al., "Hybridization of Alternating Cationic/Anionic Oligonucleotides to RNA Segments", Nucleosides & Nucleotides, 13 (6&7):1597-1605 (1994).

P. Juteau, et al., "Analysis of the bacterial community inhabiting an aerobic thermophilic sequencing batch reactor (AT-SBR) treating swine waste", Applied Microbiology and Biotechnology (2005) 66:115-122.

R. Letsinger, et al., "Cationic oligonucleotides", J. Am. Chem. Soc., 110:4470-4471 (1988).

R. Letsinger, et al., "Effects of pendant groups at phosphorus on binding properties of d-ApA analogues", Nucl. Acids Res., 14 (8):3487-3499 (1986).

R. Letsinger, "Phosphoramidate Analogs of Oligonucleotides," J. Org. Chem., 35 (11):3800-3803 (1970).

D. Lockhart, et al., "Expression monitoring by hybridization to high-density oligonucleotide arrays", Nature Biotechnology (1996) 14:1675-1680.

C. Lozupone, et al., "UniFrac: a new phylogenetic method for comparing microbial communities", Applied and Environmental Microbiology (2005) 71 (12):8228-8235.

C. Lozupone, et al., "UniFrac—an online tool for comparing microbial community diversity in a phylogenetic context", BMC Bioinformatics (2006) 7, 371. (8 pages).

J. Maddry, et al., "Ch. 3: Synthesis of Nonionic Oligonucleotide Analogues", ASC Symposium Series 580, *Carbohydrate Modifications in Antisense Research*, pp. 40-51 (1994).

M. Mag, et al, "Synthesis and selective cleavage of an oligodeoxynucleotide containing a bridged internucleotide 5'-phosphorothioate linkage", Nucleic Acids Res., 19 (7):1437-1441 (1991).

(56) References Cited

OTHER PUBLICATIONS

U. Maskos, et al., "Oligonucleotide hybridisations on glass supports: a novel linker for oligonucleotide synthesis and hybridisation properties of oligonucleotides synthesised in situ", Nuc. Acids. Res., (1992) 20 (7):1679-1684.

L. McBride, et al., "An investigation of several deoxynucleoside phosphoramidites useful for synthesizing deoxyoligonucleotides", Tetrahedron Lett. 24 (3):246-248 (1983).

K. McGrath, et al., "Isolation and analysis of mRNA from environmental microbial communities", J. Microbiol. Methods (2008) 75: 172-176.

C. Meier, et al., "Peptide Nucleic Acids (PNAs)—Unusual Properties of Nonionic Oligonucleotide Analogues", Angew. Chem. Int. Ed. Engl., 31 (8):1008-1010 (1992).

J. Ng, et al. "A spatially addressable bead-based biosensor for simple and rapid DNA detection", Biosensors & Bioelectronics, 23:803-810, (2008).

A. Nocker, et al., "Use of Propidium Monoazide for Live/Dead Distinction in Microbial Ecology", (2007), Applied and Environmental Microbiology, 73 (16): 5111-5117.

R. Pauwels, et al., "Biological Activity of New 2-5A Analogues", Chemica Scripta, 26:141-145 (1986).

A. Pease, et al., "Light-generated oligonucleotide arrays for rapid DNA sequence analysis", Proc. Natl. Acad. Sci. U.S.A. (1994) 91:5022-5026.

R. Rawls, "Optimistic About Antisense", C & E News, (Jun. 2, 1997), pp. 35-39.

H. Rawsthorne, et al., "The presence of *Saccharomyces cerevisiae* DNA in various media used to propagate yeasts and its removal by ethidium monozaide" (2009), Letters in Applied Microbiology, 49: 652-654.

S.-K. Rhee, et al., "Detection of Genes Involved in Biodegradation and Biotransformation in Microbial Communities by Using 50-Mer Oligonucleotide Microarrays", Appl. Environ. Microbiol. (2004) 70 (7):4303-4317.

K. Rudi, et al. "Use of Ethidium Monoazide and PCR in Combination for Quantification of Viable and Dead Cells in Complex Samples", Applied and Environmental Microbiology, (2005), 71(2): 1018-1024.

H. Sawai, et al., "Synthesis and Properties of Oligoadenylic Acids Containing 2'-5' Phosphoramide Linkage", Chem. Lett., 805-808 (1984).

M. Schena, et al., "Quantitative Monitoring of Gene Expression Patterns with a Complementary DNA Microarray", Science (1995) 270:467-470.

M. Sprinzl, et al., "Enzymatic Incorporation of ATP and CTP Analogues into the 3' End of tRNA", Eur. J. Biochem., 81:579-589 (1977).

J. Thompson, et al., "CLUSTAL W: improving the sensitivity of progressive multiple sequence alignment through sequence weighting, position-specific gap penalties and weight matrix choice", Nucleic Acids Res. (1994) 22 (22):4673-4680.

G. Von Kiedrowski, et al., "Parabolic Growth of a Self-Replicating Hexadeoxynucleotide Bearing a 3'-5'-Phosphoamidate Linkage", Angew. Chem. Intl. Ed. English, 30:423-426 (1991).

L. Wu, et al., "Microarray-Based Analysis of Subnanogram Quantities of Microbial Community DNAs by Using Whole-Community Genome Amplification", Appl. Environ. Microbiol. (2006) 72 (7), 4931-4941.

E. Yergeau, et al., "Environmental microarray analyses of Antartic soil microbiol communities", ISME J., (2009) 3:340-351.

L. Zhang, et al., "A model of molecular interactions on short oligonucleotide microarrays", Nat. Biotechnol. (2003), 21 (7):818-821.

Zhou, et al., "DNA recovery from soils of diverse composition", Appl. Environ. Microbiol. (1996) 62 (2):316-322.

\* cited by examiner

METHODS FOR DETECTING AND QUANTIFYING VIABLE BACTERIAL ENDO-SPORES

CROSS REFERENCE TO RELATED APPLICATIONS

This application is related and claims priority to U.S. Provisional Application entitled "Rapid fluorescent detection of viable bacterial endospores" Ser. No. 61/351,238, filed on Jun. 3, 2010 herein incorporated by reference in its entirety. This application is also related and claims priority to U.S. Provisional Application entitled "PMA-Phylochip, a DNA microarray to elucidate viable microbial community structure", Ser. No. 61/441,820, filed on Feb. 11, 2011, herein also incorporated by reference in its entirety.

STATEMENT OF GOVERNMENT GRANT

The invention described herein was made in the performance of work under a NASA contract, and is subject to the provisions of Public Law 96-517 (35 USC 202) in which the Contractor has elected to retain title.

FIELD

The present disclosure relates to endospores. In particular the present disclosure related to methods and systems to detect viable bacterial endospore.

BACKGROUND

Bacterial endospores can survive without nutrients. They are resistant to ultraviolet radiation, desiccation, high temperature, extreme freezing and chemical disinfectants. Common anti-bacterial agents that work by destroying vegetative cell walls don't work on endospores. Endospores are commonly found in soil and water, where they may survive for long periods of time.

Development of a rapid and/or sensitive method for detecting and in particular quantitatively detecting bacterial endospores has been challenging.

SUMMARY

Provided herein, are methods and systems for detecting viable bacterial endospores in a sample, which in several embodiments allow quantification of the detected viable endospores. Methods and systems herein described are based on detection of a first form of nucleic acid which is not comprised within the viable bacterial endospore, performed in connection with detection of a second form of nucleic acid which is comprised within the viable bacterial endospores According to a first aspect, a method and system for detecting viable bacterial endospores in a sample is described. The method comprises contacting the sample with an agent, the agent being able to label the first form of nucleic acid to produce a first signal. The method further comprises detecting the first signal from the sample, and treating the sample under a suitable condition to convert the second form of nucleic acid into the first form of nucleic acid, to produce a treated sample. The method further comprises contacting the treated sample with the agent able to label the first form of nucleic acid to produce a second signal, and detecting a second signal from the sample. The method also comprises subtracting the first signal from the second signal to detect viable endospores in the sample.

According to a second aspect, a method and system of detecting viable bacterial endospores in a sample is described. The method comprises contacting the sample with an agent, the agent being able to label the first form of nucleic acid in the sample and interfere with amplification of the labeled first form of nucleic acid. The method further comprises treating the sample to produce an extract, the treating performed for a time and under condition to allow extraction from the sample of a nucleic acid comprising the first form of nucleic acid and the second form of nucleic acid, and performing nucleic acid amplification of the extract. The method further comprises detecting the amplification of extracted nucleic acid and detecting viable endospores in the sample based on the detected amplification product.

According to a third aspect, a method and system for quantitatively detect viable bacterial endospores in a sample is described. The method comprises contacting the sample with an agent able to label the first form of nucleic acid to produce a first signal. The method further comprises detecting the first signal from the sample following the contacting, and treating the sample under a suitable condition to convert the second form of nucleic acid into the first form of nucleic acid, to produce a treated sample. The method also comprises contacting the treated sample with the agent able to label the first form of nucleic acid to produce a second signal and detecting the second signal from the sample. The method further comprises subtracting the first signal from the second signal, comparing the subtracted signal to a look-up table, the look-up table comprising pre-determined signals associated to a quantity of the viable bacterial endospore, and determining the quantity of viable bacterial endospores in the sample.

According to a fourth aspect, a method and system for quantitatively detecting viable bacterial endospores in a sample is described. The method comprises contacting the sample with an agent, able to label the first form of nucleic acid in the sample and interfere with amplification of the labeled first form of nucleic acid. The method further comprises treating the sample to provide an extract, the treating performed for a time and under conditions allowing extraction of the first form of nucleic acid and the second form of nucleic acid from the sample, and amplifying the extracted nucleic acid. The method further comprises detecting a quantity of the amplification of extracted nucleic acid following nucleic acid amplification, comparing the detected quantity of the amplification to a look-up table, which comprises pre-determined quantities of amplification associated to quantities of viable bacterial endospores, and determining a quantity of viable bacterial endospores in the sample.

The methods herein described allow in several embodiments rapid and sensitive detection and quantification of viable endospores from a sample containing a mixture of entities, including but not limited to, viable and/or dead bacterial cells and/or endospores. The methods herein described also allow in several embodiments detection and quantification of viable bacterial endospores from samples of both low and high biomass. In particular, the methods herein described allow in several embodiments detection and quantification of viable bacterial endospores from a sample containing as few as 10 endospores, or from samples containing $10^1$-$10^8$ spores/ml.

The methods and systems herein described can be used in connection with applications wherein detection of viable endospore is desired, including but not limited to medical application, biological analysis and diagnostics including but not limited to clinical applications, food industry applications (e.g. validating food processing technologies, and/or sterility and quality of food), pharmaceutical and medical equipment industries applications, (e.g. directed to spores detection as a marker for sterility), biosensors for bacterial detection in medical clinics, and microbial detection systems employed by governmental agencies, (e.g. directed to validating sterilization processes of USPS postal products, equipment and facilities, water treatment systems, and various public health applications).

The details of one or more embodiments of the disclosure are set forth in the accompanying drawings and the description below. Other features, objects, and advantages will be apparent from the description and drawings, and from the claims

BRIEF DESCRIPTION OF THE DRAWINGS

The accompanying drawings, which are incorporated into and constitute a part of this specification, illustrate one or more embodiments of the present disclosure and, together with the detailed description and examples sections, serve to explain the principles and implementations of the disclosure.

DETAILED DESCRIPTION

Figure 1:
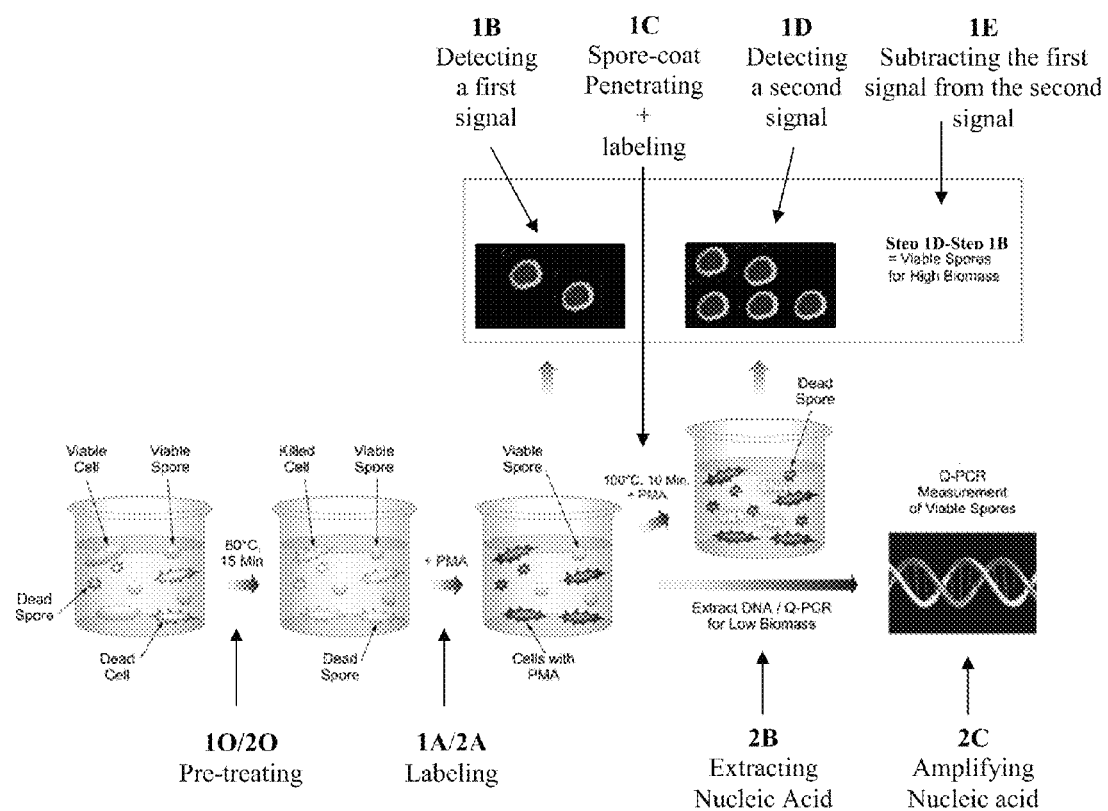
FIG. 1 shows a schematic representation of exemplary embodiments of the methods and systems herein described. A first exemplary method 1 is identified by the schematic illustration of steps 1A→1B→1C→1D→1E and is possibly inclusive of the optional step 1O. A second exemplary method 2 is identified by the schematic illustration of steps 2A→2B→2C and is possibly inclusive of the optional step 2O.

Provided herein, are methods for detecting and possibly quantifying viable bacterial endospores in a sample.

The terms "detect" or "detection" as used herein indicates the determination of the existence, presence or fact of a target in a limited portion of space, including but not limited to a sample, a reaction mixture, a molecular complex and a substrate. The "detect" or "detection" as used herein can comprise determination of chemical and/or biological properties of the target, including but not limited to ability to interact, and in particular bind, other compounds, ability to activate another compound and additional properties identifiable by a skilled person upon reading of the present disclosure. The detection can be quantitative or qualitative. A detection is "quantitative" when it refers, relates to, or involves the measurement of quantity or amount of the target or signal (also referred as 'quantitation'), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

The term "bacteria" as used herein refers to single-cell prokaryotic microorganism species typically of a few micrometers in length and a wide range of shapes, including but not limited to Gram-negative bacteria and Gram-positive bacteria. The term "Gram-negative bacteria" refers to bacterial species that do not retain crystal violet dye in the Gram staining protocol. In contrast, the wording "Gram-positive bacteria" refers to bacterial species that are stained dark blue or violet by Gram staining. Several Gram-positive bacteria form endospores, including but not limited to the genus *Bacillus* and *Clostridium*. *Bacillus* bacteria are rod-shaped, aerobic or facultative, endospore-forming bacteria. The spores of *Bacillus* are particularly hard to lyse by either physical or chemical means due to its structure and composition. A spore core is surrounded by the core wall, a cortex and a spore coat.

The term "bacterial endospore" as uses herein indicates a dormant and temporarily non-reproductive structure produced by certain bacteria, the formation of which is usually triggered under an unfavorable condition for bacteria, such as a lack of nutrients. The endospore typically consists of the bacterium's DNA and part of its cytoplasm, surrounded by a very tough outer coating, known as the endospore coat. Generally, when the environment becomes more favorable, the endospore can germinate to the metabolically active state, known as the vegetative state. Examples of bacteria able to form endospores comprise bacteria of the genus *Bacillus* and *Clostridium*.

The term "viable" as used herein with reference to bacteria and endospore indicates a bacteria or endospore having a metabolic rate compatible with life. Exemplary viable bacteria comprise normal and intact bacterial cells and bacteria in a viable but nonculturable (VBNC) state, wherein the bacteria is in a state of very low metabolic activity and do not reproduce, but has the ability to become culturable once resuscitated (e.g under a favorable growth condition). Exemplary viable endospores comprise endospores capable of germinating under appropriate condition and endospores that are in a VBNC state. Bacteria and endospores can enter the VBNC state as response to for examples, stress, due to adverse nutrient, temperature, osmotic, oxygen, and light conditions.

The term "sample" as used herein indicates a limited quantity of something that is indicative of a larger quantity of that something, including but not limited to solids and/or fluids from a biological environment, specimen, cultures, tissues, commercial recombinant proteins, synthetic compounds or portions thereof. Exemplary samples in the sense of the current disclosure include an environment sample collected from water, soil, air or the outer space, samples collected from a surface of a facility, equipment or system, food or pharmaceutical preparation.

In several embodiments, methods and systems are described that can be used for detecting viable bacterial endospores in a sample are described. In methods and systems detection is performed based on detection of two forms of nucleic acids in the sample: a first form of nucleic acid which is not comprised in the viable endospores, and a second form of nucleic acid which is comprised within the viable endospores. The first form of nucleic acid comprises nucleic acid included in a structure other than a viable endospore (e.g. non-viable endospore, dead bacterial cell) or present in the sample outside any cell and/or endospore structure (e.g.

unbound nucleic acid sequences in free solution). The second form of nucleic acid is formed instead by nucleic acid within the viable endospore.

The term "nucleic acid" as used herein indicates a polymeric form of nucleotides of any length, either ribonucleotides or deoxyribonucleotides, that comprise purine and pyrimidine bases, or other natural, chemically or biochemically modified, non-natural, or derivatized nucleotide bases. Nucleic acids of the embodiments of the current disclosure include Deoxyribonucleic acid (DNA), ribonucleic acid (RNA), or DNA copies of RNA (complementary DNA or cDNA), which may be isolated from natural sources, recombinantly produced, or artificially synthesized. The nucleic acids may exist as single-stranded or double-stranded and any chemical modifications thereof, provided only that the modification does not interfere with amplification of selected nucleic acids. For example, the backbone of the nucleic acid can comprise sugars and phosphate groups or modified or substituted sugar or phosphate groups, and a nucleic acid may comprise modified nucleotides, such as methylated nucleotides and nucleotide analogs.

The methods herein described allow, in several embodiments, qualitative and/or quantitative detection of viable bacterial endospores in a sample through use of agents are capable of selective binding with respect to the two forms of nucleic acid herein described.

The term "agent" as used herein indicates a molecule, such as a ligand, or a chemical reagent that is capable of interacting with a nucleic acid molecule, such as a DNA molecule. The term "ligand" as used herein indicates a molecule that is recognized by a particular receptor. Exemplary receptors for a ligand in the sense of the current disclosure include, but are not restricted to polynucleotides and nucleic acids. The term "reagent" as used herein indicates a substance, a compound or a mixture that is added to a system in order to bring about a chemical reaction or to examine whether a reaction occurs. Exemplary types of interaction between the agent and nucleic acids include covalent binding, electrostatic binding and intercalating.

The term "covalent binding" indicates a process of formation of a chemical bonding that is characterized by sharing of pairs of electrons between atoms, known as the covalent bond. Covalent bonding indicates a stable balance of attractive and repulsive forces between atoms when the atoms share their electrons, and includes many kinds of interaction, including σ-bonding, π-bonding, metal to metal bonding, agostic interactions, and three-center two-electron bonds. The term "electrostatic binding" indicates association between two oppositely charged entities.

The term "intercalating" as used herein indicates a process when a nucleic acid intercalating agent fit itself in between base pairs of a nucleic acid molecule. Structural and chemical properties that are characteristic of nucleic acid intercalating agents often comprise a proper molecular size, being cationic, polycyclic, aromatic, planar and hydrophobic for the following proposed mechanism of nucleic acid intercalation to take place: In aqueous isotonic solution, a cationic intercalating agent is attracted electrostatically to the polyanionic nucleic acid molecules. The intercalating agent displaces a sodium and/or magnesium cation that surrounds the nucleic acid, forming a weak electrostatic bond with the outer surface of the nucleic acid. From this position, the intercalating agent can slide into the hydrophobic environment found between the base pairs and away from the hydrophilic outer environment surround the nucleic acid. The base pairs transiently form such openings for the entering of the intercalating agent due to energy absorbed during collision with the solvent molecules. Exemplary nucleic acid intercalating agents include propidium monoazide (PMA), ethidium monoazide bromide (EMA), ethidium bromide, berberine, proflavine, daunomycin, doxorubicin, and thalidomide.

During intercalation, the nucleic acid dynamically opens a space between its base pairs by unwinding. The degree of unwinding varies depending on the specific intercalating agent. The unwinding of the base pairs induces local structural changes to the strand, such as lengthening of the strand or twisting the base pairs. These structural modifications can lead to in vivo functional changes, such as inhibition of transcription, replication and/or repairing of the intercalated nucleic acid. For this reason, nucleic acid intercalating agents are often carcinogenic and are suitable to be used as potent mutagens. One example of such intercalating agents is ethidium bromide (EB), which is commonly used as a fluorescent dye that stains nucleic acid in molecular biology laboratories and technology, such as agarose gel electrophoresis. The chemical structure of ethidium bromide is shown below.

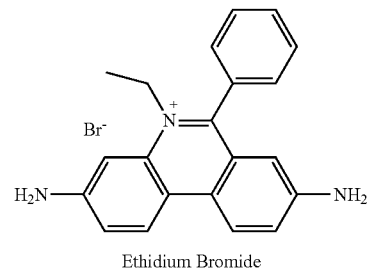

Ethidium Bromide

In embodiments of methods and systems herein described, the agent used is able to selectively bind the first form of nucleic acid in the sample.

The wording "selective", "specific" "specifically" or "specificity" as used herein with reference to the binding of a first molecule to second molecule refers to the recognition, contact and formation of a stable complex between the first molecule and the second molecule, together with substantially less to no recognition, contact and formation of a stable complex between each of the first molecule and the second molecule with other molecules that may be present. Exemplary specific bindings are antibody-antigen interaction, cellular receptor-ligand interactions, polynucleotide hybridization, enzyme substrate interactions etc. The term "specific" as used herein with reference to a molecular component of a complex, refers to the unique association of that component to the specific complex which the component is part of. The term "specific" as used herein with reference to a sequence of a polynucleotide refers to the unique association of the sequence with a single polynucleotide which is the complementary sequence. By "stable complex" is meant a complex that is detectable and does not require any arbitrary level of stability, although greater stability is generally preferred. The term "selective" "specific" "specifically" or "specificity" as used herein with reference to a chemical or biological activity of a first molecule to second molecule of a certain bacteria or group of bacteria refers to the ability of the first molecule to direct the activity towards the second molecule, together with substantially less to no activity between the first molecule and molecules that may be present of organisms other than the bacteria or group of bacteria.

Accordingly the agent used in methods and systems herein described is able to recognize, contact and form a stable complex with the first form of nucleic acid, together with substantially less to no recognition, contact and formation of a stable complex with the second nucleic acid that may be present and substantially no labeling of the second form of nucleic acid. The term "substantially" as used herein indicates an extent of that does not materially affect the parameter at issue.

In an embodiment, the agents selectively penetrate compromised bio-membrane, such as cell membrane of dead bacteria and spore-coat of dead endospores, but are substantially impermeable to intact bio-membrane of viable cells and endospores. Only after penetrating through bio-membrane of bacteria, the agent is able to get access to and label bacterial nucleic acids.

A schematic illustration of exemplary embodiments of the methods and systems herein described is reported in FIG. 1. According to a first exemplary embodiment (FIG. 1 step 1A to 1E), the method comprises labeling a sample with an agent (for example with PMA) (FIG. 1 step 1A), detecting a first signal (FIG. 1 step 1B), treating the sample to convert the second form of nucleic acid and labeling the sample (FIG. 1 step 1C), detecting a second signal (FIG. 1 step 1D), and subtracting the detected signals to detect the viable endospores (FIG. 1 step 1E). According to a second embodiment (FIG. 1 Steps 2A to 2C), the method comprises labeling the sample (FIG. 1 step 2A), extracting nucleic acid from the sample (FIG. 1 step 2B), and amplifying the extracted nucleic acid (for example, with qPCR). (FIG. 1 step 2C). In some embodiments, each of the above method can further comprises pre-treating the sample to inactivate, and in particular kill, viable bacterial cells in the sample, for example by heating at about 85° C. for about 15 minutes (FIG. 1 Step 1O and step 2O) before the labeling step (FIG. 1 step 1A/2A). Additional embodiments based on the exemplary illustration of FIG. 1 are identifiable by a skilled person.

As illustrated in the exemplary schematics of FIG. 1, in some embodiments, the agent can be conjugated with a labeled molecule, such as a probe, which can produce a signal. In particular, methods herein described allow, in several embodiments, qualitative and/or quantitative detection of viable bacterial endospores in a sample through detection of signals from the sample produced by a label (see FIG. 1 steps 1A to 1E).

The term "labeled molecule" or "probe" as used herein as component of a complex or molecule refer to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like that are identifiable by a skilled person. As a consequence, the wording "signal" or "labeling signal" as used herein indicates the signal emitted from the agent itself or the probe conjugated to the agent that allows detection of the agent and consequently the labeled target, including but not limited to radioactivity, fluorescence, chemiluminescence, production of a compound in outcome of an enzymatic reaction and the like that are identifiable by a skilled person.

In particular detection of signals can be performed in several embodiments of the methods and systems herein described, from a labeled first form of nucleic acid as herein described.

In embodiments herein described the sample is contacted with an agent, able to label the first form of nucleic acid and producing a corresponding first signal. In some embodiments, the same or a corresponding sample can then be treated under a suitable condition to convert the second form of nucleic acid comprised in viable bacterial endospores into the first form of nucleic acid. The method further comprises contacting the treated sample with an agent able to selectively label the first form of nucleic acid to provide a second signal, detecting the second signal from the sample, subtracting the first signal from the second signal to detect the viable endospores in the sample.

Figure 2:
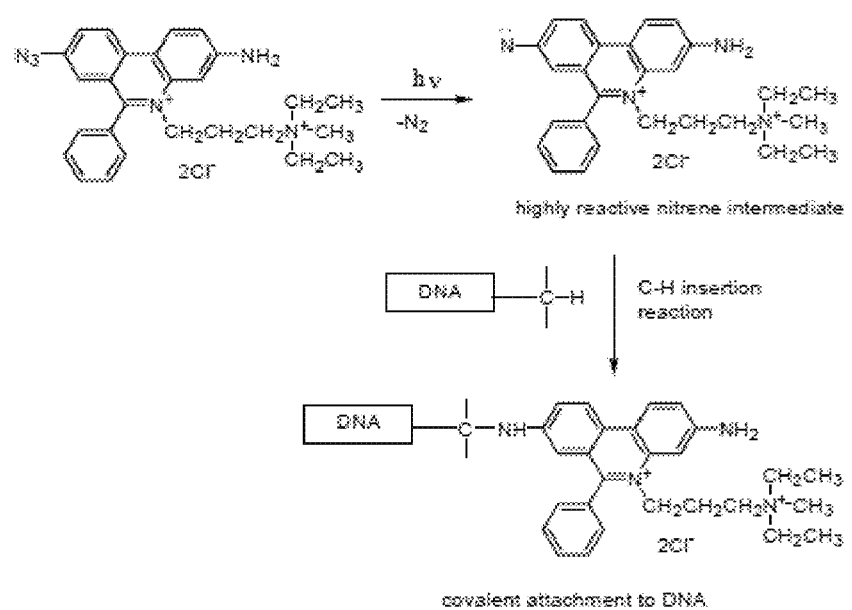
FIG. 2 shows a reaction scheme illustration an exemplary nucleic acid modification performed by an exemplary agent suitable in methods and systems herein described.

As further illustrated in the schematics of FIG. 1 (see steps 2A to 2C), in some embodiments, the agent comprises a nucleic acid intercalating agent, able after intercalating into a nucleic acid molecule, to also covalently link to the molecule, thereby interferes with amplification of the molecule and in particular with PCR amplification. For example, PMA is a high affinity photo-reactive DNA binding dye, which is weakly fluorescent by itself but becomes more fluorescent after binding to nucleic acids. PMA preferentially binds dsDNA with high affinity. Upon photolysis, the photo-reactive azido group of the molecule is converted to a highly reactive nitrene radical, which readily reacts with any hydrocarbon moiety at the binding site to form a stable covalent nitrogen-carbon bond, thus resulting in permanent DNA modification which prevents PCR amplification of the DNA molecule (see FIG. 2). The chemical structure of PMA is shown below. Another fluorescent intercalating agent that covalently binds to and interferes with PCR amplification of nucleic acids is ethidium monoazide bromide (EMA), the chemical structure of which is also shown below. A person skilled in the art may recognize other types agents, including nucleic acid intercalating agents, which may be used in the method herein disclosed.

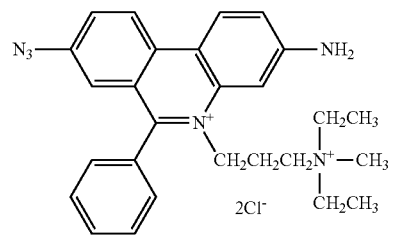

Ethidium Monoazide Bromide (EMA)

Propidium Monoazide (PMA)

Accordingly, the methods herein described also allow, in several embodiments, detection of viable bacterial endospores in a sample through amplification techniques such as real-time quantitative PCR (qPCR).

The term "real-time PCR", "real-time quantitative PCR" or "qPCR" as used herein indicate a laboratory technique based on the polymerase chain reaction (PCR), which is used to amplify and simultaneously quantify a target DNA molecule. For one or more specific sequence in a DNA sample, real-time PCR enables both detection and quantification. The quantity can be either an absolute number of copies of the amplified DNA molecules or a relative amount when normalized to the DNA template input or additional normalizing genes or DNA molecule. The real-time PCR procedure follows the general principle of polymerase chain reaction with a key feature that the amplified DNA is detected as the reaction progresses i.e. in real time. Two common methods for detection of products of DNA amplification in real-time PCR are detecting non-specific fluorescent dyes that intercalate with any double-stranded DNA and detecting sequence-specific DNA probes consisting of oligonucleotides that are labeled with a fluorescent reporter which permits detection only after hybridization of the probe with its complementary DNA target. Real-time PCR can be combined with reverse transcription to quantify RNA molecule present in a sample.

In particular some embodiments, methods herein described comprise contacting the sample with an agent able to label the first form of nucleic acid in the sample and interfere with amplification of the labeled first form of nucleic acid. The method further comprises treating the sample following the contacting for a time and under condition suitable to extract nucleic acid from the sample and then performing amplification of the extract acid (e.g. using real-time quantitative PCR). The method further comprises detecting the amplification product to detect viable endospores in the sample.

In some embodiments, the agent can be a nucleic acid intercalating agent, such as PMA or EMA.

As also illustrated in the exemplary schematic illustration of FIG. 1 (see step 1O/2O), in some embodiments the method can comprise pre-treating the sample under a suitable conditions which inactivate and in particular kill viable bacterial cells in the sample but minimizes effects on viable endospores.

In particular, in some embodiments, the pretreating can be performed by heating the sample to about 85° C. for about 15 minutes. Additional approaches, including for example use of UV or chemical agents that are suitable for the pre-treating are identifiable by a skilled person and could be used in the alternative or in combination with the heating or one with the other.

In several embodiments, contacting a sample with an agent can be performed through mixing the sample with the agent, for example, in a solution. In other embodiments, the contacting is performed through spraying the agent, for example in a fluid or powder form, onto a surface where the sample is located and distributed.

The term "solution" as used herein comprises a single-phase or multiple phase liquid system, also including colloids and suspensions. Exemplary solutions include homogeneous mixture composed of two or more substances, where typically a solute is dissolved in another substance, known as a solvent. Additionally exemplary solutions in the sense of the disclosure include non-homogeneous mixtures such as chemical mixture in which one substance is dispersed evenly throughout another (colloids) and heterogeneous fluid containing solid particles that are sufficiently large for sedimentation (suspensions).

In some embodiments, detecting a signal can be performed through image acquisition. In other embodiments, detecting a signal is performed through microscopy or spectroscopy.

In some embodiments, the detected signal can be quantified through measuring a signal intensity, for example, brightness of a fluorescent image, which also allows comparison and subtraction of signals obtained by multiple rounds of detections.

In various embodiments of the methods herein described comprises treating a sample under a suitable condition to convert the second form of nucleic acid to the first form of nucleic acid. Exemplary treatments can compromise the integrity and in particular remove or disintegrate spore-coat of the viable endospores in the sample and at the same time maintains integrity of the nucleic acid comprised within the viable endospores, so as to facilitate penetration of the agents into the viable endospores and labeling the nucleic acid comprised therein. For example according to some embodiments, since autoclaving viable bacterial endospores, (e.g. exposure to 121° C. for 15 to 20 minutes) results in partial degradation of the endospore DNA (see e.g. Example 3), the treating is performed by heating the sample to a temperature lower than 121° C.

Particularly, in some embodiments, the treating can be performed by heating the sample to a temperature within the range of 90 to 100° C., preferably for a duration of between 5 to 30 minutes. See Example 4.

In some embodiments, the treating can be performed by ultraviolet (UV) radiation (see e.g. Example 5). The term "UV radiation" or "UV light" as used herein indicates electromagnetic radiation with a wavelength shorter than that of visible light, but longer than X-rays, in the range of 10 nm to 400 nm, and energy from 3 eV to 124 eV.

Accordingly, in some embodiments, the treating can be performed by exposing the sample to UV radiation. In particular, in some embodiments, the treating is performed by exposing the sample to 245 nm UV radiation of a dose, preferably between 0.2-3 KJ/m$^2$ In some embodiments, the treating can be performed by contacting viable bacterial endospores to urea, e.g. a urea-containing buffer results in disintegration of spore-coat (See Example 6).

Accordingly, in some embodiments, the treating can be performed by exposing the sample to a buffer comprising urea. In particular, in some embodiments, the buffer comprises about 8M urea. In some embodiments, the buffer further comprises about 5 mM cyclohexylaminoethane sulfonic acid, about 50 mM dithioerythritol and about 0.8% sodium dodecyl sulfate. In some embodiments, the buffer further comprises about 5 mg lysozyme. In some embodiments, the buffer is adjusted to a pH of about 9.8.

Additional procedures suitable for performing the treating according to the various embodiments of methods and systems herein described comprise various combination of heating, UV treatment and/or use of chemicals as will be understood by a skilled person in view of the present disclosure.

In some embodiments, the methods and systems herein described allow quantitative detection of viable bacterial endospores in a sample are described. The term "quantify" or "quantification" as used herein indicates processes relate to or involve the measurement of quantity or amount of the target or signal (also referred as quantitation), which includes but is not limited to any analysis designed to determine the amounts or proportions of the target or signal.

The methods herein described allow, in several embodiments, quantifying viable bacterial endospores in the sample through detection of signals from the sample. The method comprises contacting the sample with an agent, the sample comprising a first form of nucleic acid and a second form of nucleic acid, the agent being able to label the first form of nucleic acid in the sample and produce a signal, wherein the second form of nucleic acid consists nucleic acid comprised in viable bacterial endospores in the sample. The method further comprises detecting a first signal from the sample, treating the sample under a suitable condition to convert the second form of nucleic acid comprised in the viable bacteria endospores into the first form of nucleic acid, thus to produce a treated sample contacting the treated sample with the agent again and detecting a second signal from the sample. The method further comprises subtracting the first signal from the second signal, comparing the subtracted signal to a look-up table, the look-up table comprising pre-determined signal associated to numbers of viable bacterial endospores, and determining a number of viable bacterial endospores in the sample.

The methods herein described allow, in several embodiments, quantifying viable bacterial endospores in the sample through real-time qPCR. The method comprises contacting the sample with an agent, the sample comprising a first form of nucleic acid and a second form of nucleic acid, the agent being able to label the first form of nucleic acid in the sample and interfere with PCR amplification of the labeled first form of nucleic acid, wherein the second form of nucleic acid consists nucleic acid comprised in viable bacterial endospores in the sample. The method further comprises extracting the first form of nucleic acid and the second form of nucleic acid from the sample, and amplifying the extracted nucleic acid using real-time quantitative PCR. The method further comprises detecting a quantity of the amplification of extracted nucleic acid, comparing the detected quantity to a look-up table, which comprises pre-determined quantities of amplification associated to numbers of viable bacterial endospores, and determining a number of viable bacterial endospores in the sample.

The look-up table herein described can be any form and format of arrangement of pre-determined relationship and correspondence between two or more changing parameters. For example, a look-up table can be in the format of a standard curve, a table or a data base. Exemplary parameters that can be included in a look-up table according to the current disclosure includes pre-determined amount of nucleic acid with relation to an amount and/or number of bacterial endospores, pre-determined intensity of signals detected from a sample with relation to an amount and/or number of viable bacterial endospores in the sample, pre-determined copy number of qPCR amplification of nucleic acid extracted from a sample with relation to an amount and/or number of viable bacterial endospores in the sample. A skilled person would be able to identify other suitable parameters and ways of determining such parameters so to construct or modify a look-up table in a suitable format upon reading the current disclosure.

The agents and other reagents herein described can be provided as a part of systems to perform any assay, including any of the assays described herein. The systems can be provided in the form of kits of parts. In a kit of parts, the agents and other reagents to perform the assay can be comprised in the kit independently. The agents and other reagents can be included in one or more compositions, and each agent and reagent can be in a composition together with a suitable vehicle.

Additional components can include labels reference standards, and additional components identifiable by a skilled person upon reading of the present disclosure. In particular, the components of the kit can be provided, with suitable instructions and other necessary reagents, in order to perform the methods here described. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

EXAMPLES

The methods and systems herein disclosed are further illustrated in the following examples, which are provided by way of illustration and are not intended to be limiting.

In particular, the following examples illustrate exemplary embodiments of the methods and systems for qualitative and/or quantitative detecting viable bacterial endospores in a sample. A person skilled in the art will appreciate the applicability and the necessary modifications to adapt the features described in detail in the present section, to additional solutions, methods and systems according to embodiments of the present disclosure.

The following materials and methods where used in the experiments illustrated in this section Quantitative Real-Time PCR (qPCR):

The current protocol that has been chosen for use with qPCR is a SYBR Green I dye format. Universal Primers targeting the 16S rRNA (1369F: CGG TGA ATA CGT TCY CGG (SEQ ID NO:1); 1492R: GGW TAC CTT GTT ACG ACT T (SEQ ID NO:2)) gene sequence will be used for all organisms. One µL of purified DNA will be amplified with 16S rRNA primers in a 25 µL hot-start PCR reaction mixtures for:

Stage 1: Hold 95° C. for 120 sec
Stage 2: 3-Temp Cycle Repeat for 40 times
95° C. for 15 sec
55° C. for 60 sec with optics ON
72 C for 20 sec
Stage 3: Melt Curve 60° C. to 95° C. at 0.2° C./sec with Optic Ch1 ONThe qPCR protocol has been adapted from Cooper, M., LaDuc, M. T., Probst, A., Vaishampayan, P., Stam, C., Benardini, J. N., Piceno, Y. M., Andersen, G. L., and Venkateswaran, K. (2011) "Assessing the cleanliness of surfaces: Innovative molecular approaches vs. standard spore assays." *Appl Environ Microbiol*, herein incorporated by reference in its entirety.

*B. pumilus* SAFR-032 qPCR.

All quantitative PCR (qPCR) were carried out with a Cepheid Smart Cycler system (Cepheid; Sunnyvale, Calif.). *B. pumilus* specific primers targeting a 380 base-pair region of the DNA gyrase subunit B encoding gyrB gene were used for all amplifications. Reactions mixtures consisted of 2× Bio-rad iQ SYBR Green SuperMix (Bio-Rad Laboratories; Hercules, Calif.), 10 mM each forward (5'-TGA AGA TGT GCG AGA AGG CT-3') (SEQ ID NO:3) and reverse primers (5'-AGG ATC TTC CCT CTT AAC GG-3') (SEQ ID NO:4) and nuclease free water to reach a final volume of 25 µL. Amplification was achieved according to the following thermal cycling program: initial melting at 95° C. for 2 min. (1 cycle) followed by 40 cycles of melting at 95° C. for 15 sec, annealing of primers at 58° C. for 30 sec, and elongation at 72° C. for 30 seconds. The limit of detection of this assay was determined via standards whose threshold cycle ($C_T$) values were obtained from serially diluted DNA originally extracted from a spore crop at $10^8$ spores/mL. All subsequent serial dilutions were verified via plate count enumerations on TSA. Determination and selection of the threshold cycle ($C_T$) values has been adapted from Suzuki, M. T., Taylor, L. T., and DeLong, E. F. (2000) "Quantitative analysis of small-subunit rRNA genes in mixed microbial populations via 5'-nuclease assays". App. Environ. Microbiol., 66, 4605-4614, herein incorporated by reference in its entirety.

Spore Production and Enumeration.

*B. pumilus* SAFR-032 cells were grown overnight in tryptic soy broth (TSB) at 32° C. The culture was transferred to 1 L of a nutrient deficient sporulation medium, and incubated at 32° C. with shaking at 200 rpm, for 4-5 days or until sporulation is complete, as verified by phase contrast microscopy. Spores were harvested by repeated centrifugation and washing in buffer solutions at 4° C. Following washing and a final resuspension in ultrapure water, spores were heat shocked at 80° C. for 15 min, immediately cooled in an ice bath and then stored at 4° C. Enumeration was performed by pour plating with tryptic soy agar (TSA) followed by incubation at 32° C. for 48 hours. Propidium monoazide (PMA) treatment. PMA treatment of bacterial endospores with the DNA intercalating agent PMA was performed after spore coat is disturbed but before the lysozyme treatment. In particular, PMA was added at a 12.5 µg/mL concentration followed by incubation in the dark. Thereafter, spores are exposed to a 500-W halogen light for 5 minutes to intercalate PMA to the DNA. Following PMA treatment, spores are pelleted and suspended in PBS with sucrose. Lysozyme is added followed by incubation at 37° C. for 60 min. Spores are again pelleted and subjected to DNA isolation. More details of the PMA treatment of bacterial endospores can be found in Helen Rawsthorne et al., "PCR-based method using propidium monoazide to distinguish viable from nonviable *Bacillus subtilis* spores," *Applied and Environmental Microbiology* 75 (2009): pp. 2936-39, herein incorporated by reference in its entirety.

Isolation of Bacterial Endospores.

The procedure for isolating bacterial endospores can be found in La Duc, M. T., Dekas, A. E., Osman, S., Moissl, C., Newcombe, D., and Venkateswaran, K. (2007) Isolation and characterization of bacteria capable of tolerating the extreme conditions of clean-room environments. *Appl. Environ. Microbiol.*, 73, 2600-2611, herein incorporated by reference in its entirety.

Bacterial DNA Preparation.

Bacterial DNA was isolated using the Mo Bio Ultra-Clean Microbial DNA Isolation kit following manufacturer's instructions (Mo Bio Laboratories Inc.; Carlsbad, Calif.). More details of the procedure of extracting bacterial DNA from cells and endospores can be found in La Duc, M. T., Osman, S., and Venkateswaran, K. (2009) "Comparative analysis of methods for the purification of DNA from low-biomass samples based on total yield and conserved microbial diversity". *J. Rapid Meth. Auto. Microbiol.*, 17, 350-368, herein incorporated by reference in its entirety.

PMA Fluorescence Measurement.

After spore-coat removal or disintegration, the sample was treated with PMA as described above and subjected to fluorescent microscopy analysis. Fluorescence at 610 nm was acquainted and measured with a Fluorolog-3 Fluorescence spectrometer (Horiba Jobin-Yvon) under 510 nm excitation.

Example 1

PMA Intercalates with DNA and Blocks PCR Amplification

Genomic DNA isolated from *E. coli* was used as the model for the proof-of-concept that PMA can be used to intercalate DNA making it unavailable for PCR amplification. In particular, PMA was added at a 12.5 µg/mL concentration to the purified *E. coli* DNA sample followed by incubation in the dark. Thereafter, the sample was exposed to a 500-W halogen light for 5 minutes to intercalate PMA to the DNA.

Figure 3:
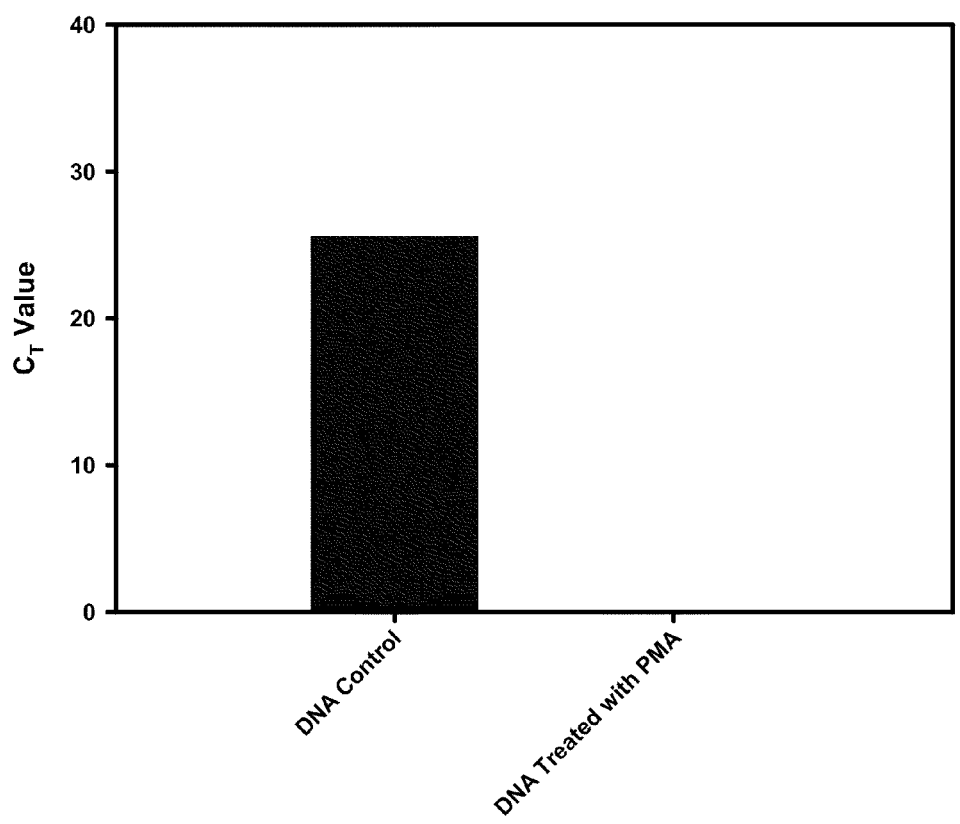
FIG. 3 shows a diagram reporting results of an exemplary amplification reaction using purified genomic DNA from *E. coli* before and after treatment with an exemplary agent herein described.

As shown in FIG. 3, isolated DNA without PMA treatment can be amplified within 26 cycles. In contrast, isolated DNA with PMA treatment was not amplified after 40 cycles (negative).

Example 2

Real-Time PCR Amplification Using DNA Extracted from Bacterial Endospores

Bacterial endospores of *Bacillus pumilus* are exposed to various treatments, before the endospore DNA was extracted and tested with real-time PCR. Specifically, the amplification target is the 16S ribosomal RNA gene. A negative control of no DNA template was included.

First, the effect of heat treatment on PCR amplification of endospore DNA was examined. In particular, DNA was extracted from SAFR-032 spores that are viable (SAFR-032 control) and after autoclaving for 15 min at 121° C. (SAFR-032 Autoclaved). As seen in the results shown in FIG. 4, DNA was not amplifiable after autoclaving, which is possibly due to a degradation of DNA, especially at the primer regions, during the autoclaving. Therefore, it is desired to expose endospores to a milder treatment, which is suitable to kill the viable endospores and leave endospore DNA intact and amplifiable using PCR.

Figure 4:
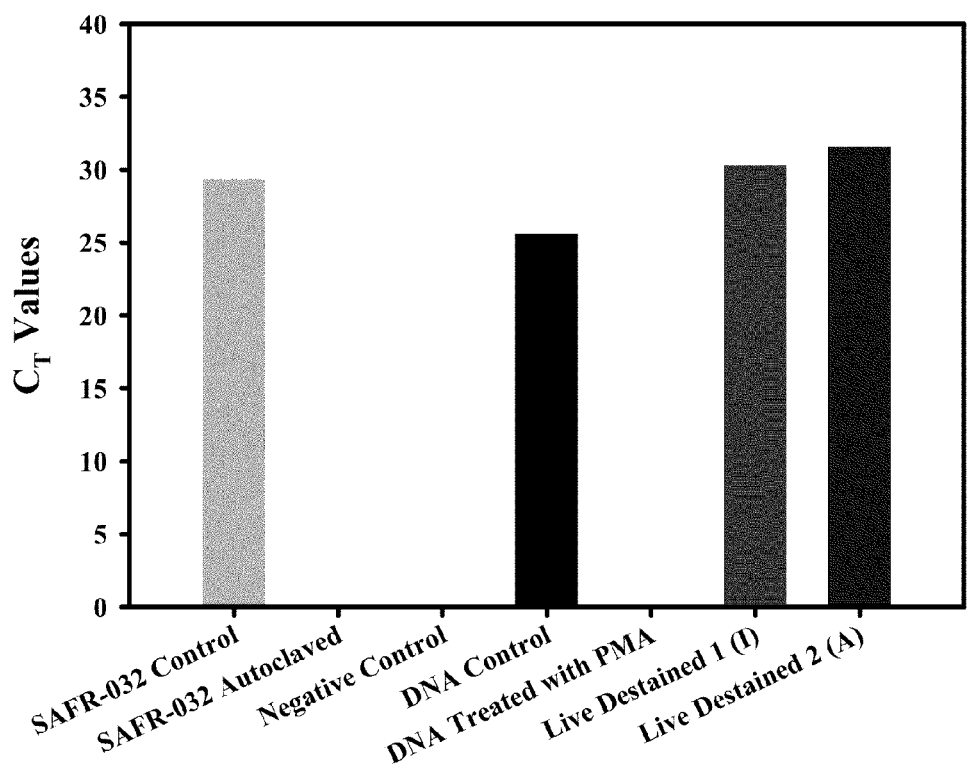
FIG. 4 shows a diagram reporting results of an exemplary amplification performed for 16s ribosomal RNA gene using DNA-intercalating agent propidium monoazide (PMA).

Next, whether PMA can intercalate with *Bacillus pumilus* DNA was examined. In particular, DNA was extracted from *Bacillus pumilus* vegetative cells (DNA control), an aliquot of which was treated with PMA (DNA treated with PMA). As shown in FIG. 4, the control DNA was amplified with 26 cycles, and the PMA treated DNA was not amplified after 40 cycles (negative). This is consistent with the results shown in FIG. 3, which suggest that PMA intercalates with and blocks PCR amplification of DNA extracted from *E. coli* and *Bacillus pumilus* cells in a similar manner.

Additionally, the effect of endospore coat on PCR amplification of endospore DNA was examined. In particular, live endospores of *Bacillus pumilus* were purified and cleaned with two chemical agents, isopropyl alcohol (I, Live Destained 1 (I)) and acetone (A, Live Destained 2 (A)), which have been shown to be able to destain and remove PMA from PMA-stained endospore coat. PMA treated live endospores were then treated with the two chemicals for 24 hours, respectively. Following the chemical treatment, endospore DNA was extracted and tested with real-time PCR. As shown in FIG. 4, cleaning endospore coat with the two chemicals does not produce a significant impact on real-time PCR amplification. A threshold of amplified copy number was reached within 30 cycles with isopropyl alcohol treatment and within 32 cycles with acetone treatment. Note that, the threshold was reached within 29 cycles for endospore DNA without chemical treatment (SAFR-032 control).

Example 3

Identification of Suitable Conditions of Treatment of Bacterial Endospores for PMA or PMA-qPCR Based Detection and Quantification of Viable Endospores A set of experiments was performed to identify the suitable treatment conditions of bacterial endospores for PMA or PMA-qPCR based detection and quantification of viable endospores. In particular, viable endospores of *Bacillus pumilus* are exposed to various treatments, before the endospore DNA was extracted and tested with real-time PCR. Specifically, the amplification target is the gyrB gene.

In order to detect and quantify viable endospores using the PMA or PMA-qPCR method, PMA need to penetrate through the endospore coat and to intercalate and blocking PCR amplifications of the endospore DNA.

Figure 5:
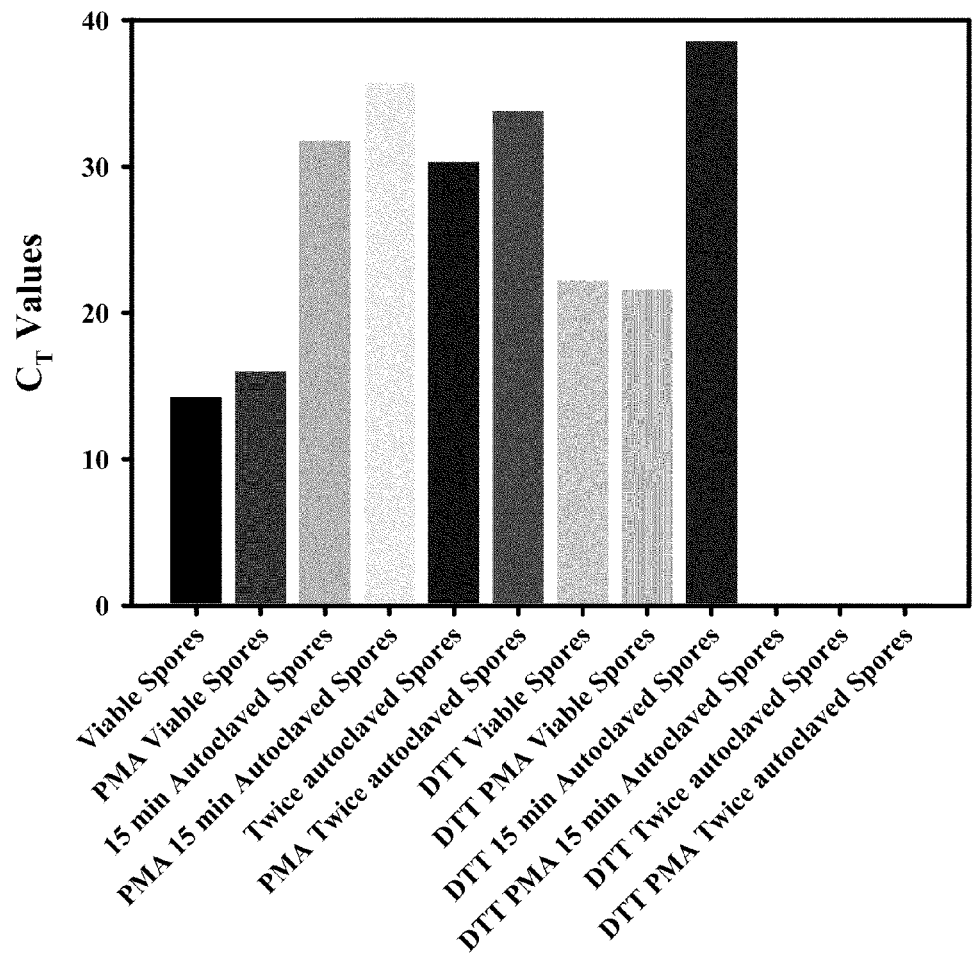
FIG. 5 shows a diagram reporting results of an exemplary amplification performed to quantify *Bacillus pumilus* endospores.

A first experiment was performed to examine whether PMA can penetrate through viable endospore coat of *Bacillus pumilus*. In particular, endospore DNA was extracted from viable endospores before (viable spores) and after (PMA viable spores) the endospores were treated with PMA. As shown in FIG. 5, no significant effect of PMA on PCR amplification was observed. Specifically, a threshold of amplified copy number was reached within 15 and 16 cycles respectively. These results indicate that viable endospores block PMA.

Therefore, it is desired to treat the viable endospores under a suitable condition, so that the endospore coat is disturbed and becomes preamble to PMA while endospore DNA is intact and remains amplifiable for PCR. To identify such treatment condition, the following experiments were performed.

Heat Treatment.

Using the method of Rawsthorne et al (2009), herein enclosed by reference in its entirety, viable *Bacillus pumilus* SAFR-032 endospores were heat treated at 121° C. for 15 min (15 min autoclaved spores) or 30 min (twice autoclaved spores). After the heat treatment, an aliquot of each of the treated samples was further treated with PMA (PMA 15 min autoclaved spores, PMA twice autoclaved spores). Then, endospore DNA was extracted from the samples and tested with real-time PCR. As shown in FIG. 5, qPCR of the PMA treated samples consistently undergo more cycles to reach a threshold of amplified copy number, which reflects partial blocking of PCR amplification by PMA. These results suggest that after the 15 min heat treatment at 121° C., PMA penetrate through the endospore coat and intercalate with endospore DNA.

Notably, real-time PCR for the 15 min autoclaved spores and the twice autoclaved spores undergoes significantly more cycles to reach the threshold when compared to real-time PCR for the viable spores. This suggests that endospore DNA after 15 min or 30 min heat treatment at 121° C. is partially degraded, which is consistent with the results shown in FIG. 5. Therefore, a milder heat treatment is preferred.

Chemical Treatment.

Viable *Bacillus pumilus* SAFR-032 endospores were chemically treated with a DTT based buffer (DTT viable spores).

After the chemical treatment, an aliquot of the treated sample was further treated with PMA (DTT PMA viable spores). Then, endospore DNA was extracted from the samples and tested with real-time PCR. As shown in FIG. 5, chemical treatment of DTT based buffer does not effect on the real-time PCR amplification. Specifically, real-time PCR for DTT viable spores and DTT PMA viable spore both reach the threshold of amplified copy number within about 20 cycles.

Combined Heat and Chemical Treatment.

Further, the heat treatment is combined with the DTT-based chemical treatment. In particular, viable *Bacillus pumilus* SAFR-032 endospores were first heat treated at 121° C. for 15 min or 30 min, followed by chemical treatment using the DTT-based buffer as described above (DTT 15 autoclaved spores, DTT twice autoclaved spores). After that, an aliquot from each of the treated sample was further treated with PMA. Then, endospore DNA was extracted from the samples and tested with real-time PCR. As shown in FIG. 5, real-time PCR for endospore samples after the combined heat and chemical treatment undergo significant more cycles to reach the threshold of amplified copy number. In particular, endospore DNA spores is amplified after more than 35 cycles for the DTT 15 min autoclaved sample, and is not amplified for DTT PMA 15 min autoclaved spores, DTT twice autoclaved spores and DTT PMA twice autoclaved spores within 40 cycles (negative).

These results suggest that the DTT-based chemical treatment is not suitable for the PMA or PMA-qPCR based detection and quantification of viable bacterial endospores.

Example 4

Identification of Suitable Conditions for Heat Treatment of Bacterial Endospores for PMA or PMA-qPCR Based Detection and Quantification of Viable Endospores As discussed in Example 2 above, endospore DNA is partially degraded during the heat treatment at 121° C., which may reduce sensitivity and/or accuracy of viable endospore detection and quantification using the subsequent PMA-qPCR method.

Therefore, a set of experiments was performed to identify milder conditions of the heat treatment that are suitable to disturbing the endospore coat, making it permeable to PMA, and at the same time keep endospore DNA intact and amplifiable using PCR.

In particular, sterile aluminum thermal death tubes were prepared by adding 1.0 mL of spore crop (undiluted spore suspensions at a concentration of approximately $10^8$-$10^9$ spores/ml) and sealed. Capillary tubes were placed in an oil bath at various temperature intervals ranging from 90-121° C. The time intervals ranged from seconds to minutes at the various temperatures. Thermal death tubes were removed from the oil bath and placed immediately in an ice bath for 5 min, and then sterilized by immersion in a 3% hypochlorite solution for 30 sec. The ends of the thermal death tube were removed and 5 ml of peptone was flushed through the tube to remove the spore sample followed by 10-fold serial dilution and plating for enumeration.

Figure 6:
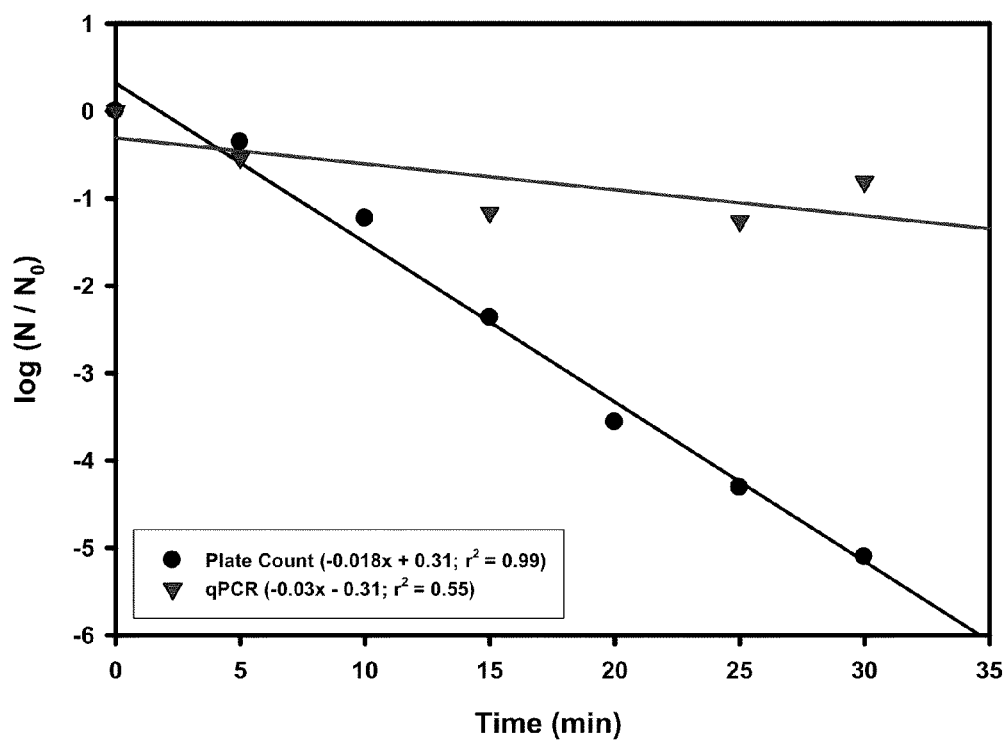
FIG. 6 shows a diagram reporting results of an exemplary heat inactivation of *Bacillus pumilus* endospores at 90° C. The D-values for plate count and qPCR are 5 and 33 min, respectively. Curves are based on the averages of all results in triplicate.

As shown in FIG. 6, heat inactivation of *Bacillus pumilus* endospores at 90° C. (as measured by the plate count) exhibits a linear relationship with the time (FIG. 6, circle). This result indicates that the heat treatment at 90° C. is challenging the cultivability of the endospores because the endospores are either killed or forced to render into the "viable but non-cultivable" (VBNC) state.

Following the heat treatment, endospore samples were treated with PMA before endospore DNA was extracted and tested with real-time PCR. As shown in FIG. 6, substantial amount of the target gyrB gene was amplified using PCR (FIG. 6 triangle), which indicates that the target gyrB was not significantly degraded during the heat treatment at 90° C. Further, a decline of amplification was observed (FIG. 6 triangle), which may reflect the intercalating effect of PMA on the endospore DNA.

These results suggest that heat treating the endospores at a lower temperature of 90° C. for a duration of up to 35 minutes could be a suitable condition for treating bacterial endospores before the PMA-qPCR based detection and quantification of viable endospores.

Example 5

Identification of Suitable Conditions of UV Treatment of Bacterial Endospore for PMA or PMA-qPCR Based Detection and Quantification of Viable Endospores A set of experiments was performed to explore alternative treatment conditions of bacterial endospores suitable for the PMA or PMA-qPCR based method.

In the following experiment, viable endospore samples (*Bacillus pumilus* SAFR-032) were exposed to various dose of UV radiation at a wavelength of 254 nm. More details about the UV treatment can be found in Newcombe, et al. 2005, "Survival of spacecraft-associated microorganisms under simulated martian UV irradiation." *Appl. Environ Microbiol*, Vol. 71, pp 8147-8156.

Figure 7:
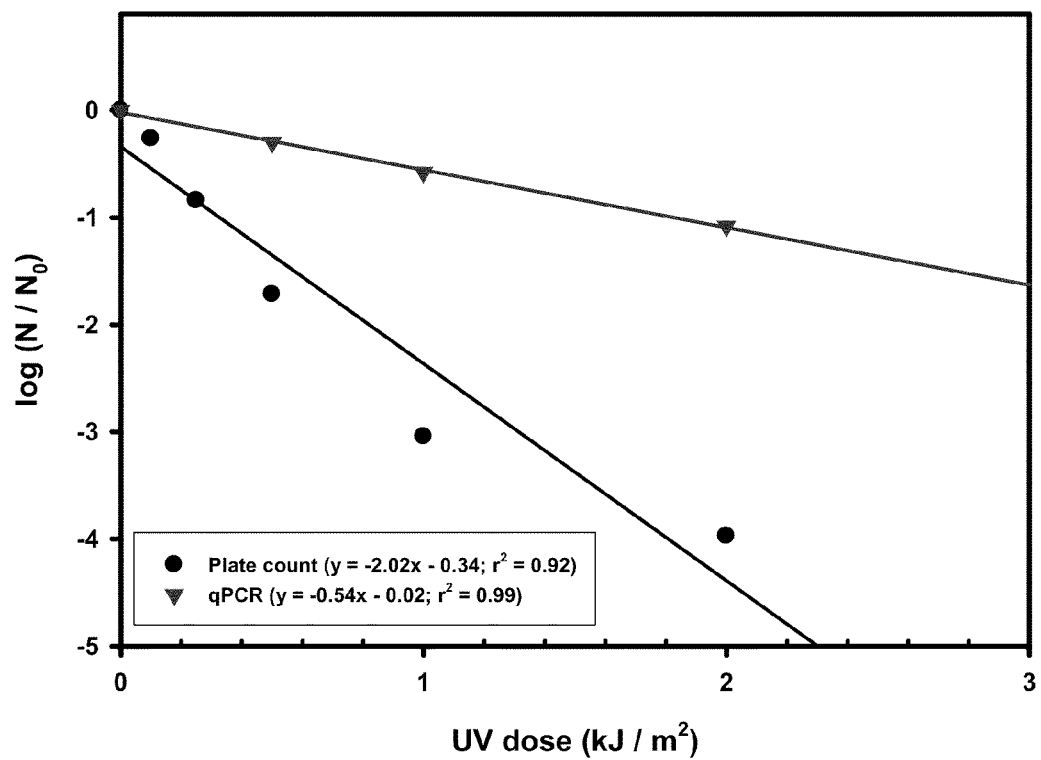
FIG. 7 shows a diagram reporting results of an exemplary UV inactivation of *Bacillus pumilus* endospores. Curves are based on the averages of all results in triplicate.

As shown in FIG. 7, UV inactivation of viable endospores (as measured by the plate count) exhibits linear relationship with the $UV_{254}$ dose (FIG. 7 circle). This result indicates that the UV treatment at 254 nm is challenging the cultivability of the endospores because the endospores are either killed or forced to render into the "viable but non-cultivable" (VBNC) state.

Following the UV treatment, endospore samples were treated with PMA before endospore DNA was extracted and tested with real-time PCR. As shown in FIG. 7, substantial amount of the target gyrB gene was amplified using PCR (FIG. 7 triangle), which indicates that the target gyrB was not significantly degraded during the UV treatment. Further, a decline of amplification was also observed (FIG. 7 triangle), which may reflect the intercalating effect of PMA on the endospore DNA.

These results suggest that exposing the endospores to 245 nm UV radiation with a dose of between 0.2-3 KJ/could be a suitable condition for treating bacterial endospores for the PMA or PMA-qPCR based detection and quantification of viable endospores.

Example 6

Identification of Suitable Conditions of Chemical Treatment of Bacterial Endospore for PMA or PMA-qPCR Based Detection and Quantification of Viable Endospores The following experiments were performed to identify suitable conditions of chemical treatment of bacterial endospores for the PMA or PMA-qPCR based detection and quantification of viable endospores.

Spore-coat disintegration was performed by pelleting and suspending the *B. pumilus* spores in spore coat extraction buffer containing urea (5 mM cyclohexylaminoethane sulfonic acid, 8M urea, 50 mM dithioerythritol, 0.8% sodium dodecyl sulfate, PH 9.8) to remove the outer spore coats. Spores were incubated at 60° C. for 1 hour in, pelleted and suspended in PBS with 25% sucrose. To promote degradation of the cortex, 50 μL of a 100 mg/mL solution of lysozyme is added followed by incubation at 37° C. for 60 min. After lysozyme treatment, spores are further pelleted and subjected to PMA treatment or DNA extraction as described above.

Example 7

Detection and Quantification of Viable Bacterial Endospores Based on PMA-Fluorescence Measurement Detection and quantification of viable bacterial endospores were performed using techniques previously illustrated in this section.

The examples set forth above are provided to give those of ordinary skill in the art a complete disclosure and description of how to make and use the embodiments of the arrangements, devices, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the paper copy of the sequence listing submitted herewith and the corresponding computer readable form are both incorporated herein by reference in their entireties.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1. Helen Rawsthorne et al., "PCR-based method using propidium monoazide to distinguish viable from nonviable *Bacillus subtilis* spores," *Applied and Environmental Microbiology* 75 (2009): pp. 2936-39.
2. Amann, R. I., Krumholz, L., and Stahl, D. A. (1990) Fluorescent-Oligonucleotide Probing of Whole Cells for Determinative, Phylogenetic, and Environmental-Studies in Microbiology. *J. Bacteriol.*, 172, 762-770.
3. Cooper, M., LaDuc, M. T., Probst, A., Vaishampayan, P., Stam, C., Benardini, J. N., Piceno, Y. M., Andersen, G. L., and Venkateswaran, K. (2011) Assessing the cleanliness of surfaces: Innovative molecular approaches vs. standard spore assays. *Appl Environ Microbiol*.
4. La Duc, M. T., Dekas, A. E., Osman, S., Moissl, C., Newcombe, D., and Venkateswaran, K. (2007) Isolation and characterization of bacteria capable of tolerating the extreme conditions of clean-room environments. *Appl. Environ. Microbiol.*, 73, 2600-2611.
5. La Duc, M. T., Osman, S., and Venkateswaran, K. (2009) Comparative analysis of methods for the purification of DNA from low-biomass samples based on total yield and conserved microbial diversity. *J. Rapid Meth. Auto. Microbiol.*, 17, 350-368.
6. Suzuki, M. T., Taylor, L. T., and DeLong, E. F. (2000) Quantitative analysis of small-subunit rRNA genes in mixed microbial populations via 5'-nuclease assays. *App. Environ. Microbiol.*, 66, 4605-4614.
7. Newcombe, D. A., A. C. Schuerger, J. N. Benardini, D. Dickinson, R. Tanner, and K. Venkateswaran. 2005. Survival of spacecraft-associated microorganisms under simulated martian UV irradiation. *Appl. Environ. Microbiol.* 71:8147-8156.

What is claimed is:

1. A method to detect a viable bacteria cell and/or endospore in a sample, the method comprising:
   contacting the sample with an agent to produce a first signal, upon the labeling of a nucleic acid from the non-viable bacterial cell and/or endospore;
   after contacting the sample with the agent to produce the first signal, detecting the first signal from the sample;
   treating the sample to render accessible nucleic acids from the viable bacterial cell and/or endospore;
   after the treating, contacting the sample with the agent to produce a second signal, the second signal produced upon labeling of the nucleic acids rendered accessible from the viable bacterial cell and/or endospore;
   after contacting the sample with the agent to produce the second signal, detecting the second signal from the sample; and
   subtracting the first signal from the second signal to detect the viable bacteria cells and/or endospore in the sample.

2. The method of claim 1, wherein the agent is selected from the group consisting of propidium monoazide (PMA), ethidium monoazide bromide (EMA), ethidium bromide, berberine, proflavine, daunomycin, doxorubicin, and thalidomide.

3. The method of claim 1, further comprises:
   pretreating the sample for a time and under conditions suitable to kill viable bacterial cells or a portion thereof before contacting the sample with the nucleic acid intercalating agent.

4. The method of claim 3, wherein the pretreating comprises heating the sample up to about 85° C. for about 15 minutes.

5. The method of claim 1, wherein the treating comprises heating the sample to a temperature within the range between about 90° C. and about 100° C.

6. The method of claim 5, wherein the heating is performed for a duration from about 5 minutes to about 30 minutes.

7. The method of claim 1, wherein the treating comprises exposing the sample to UV radiation.

8. The method of claim 7, wherein the UV radiation has a wavelength of about 245 nm.

9. The method of claim 8, wherein the UV radiation is provided in a dose of from about 0.2 to about 3 $KJ/m^2$.

10. The method of claim 1, wherein the treating comprises contacting the sample to urea.

11. The method of claim 10, wherein the urea is at a buffer concentration of about 8M.

12. The method of claim 11, wherein buffer comprises about 5 mM cyclohexylaminoethane sulfonic acid, about 50 mM dithioerythritol, about 0.8% sodium dodecyl sulfate, and about 5 mg lysozyme.

13. The method of claim 1, wherein the first signal and/or the second signal is a fluorescent signal.

14. A method to detect a viable bacteria cell and/or endospore in a sample, the method comprising:
   labeling the sample with a nucleic acid intercalating agent capable of selectively binding to a nucleic acid from non-viable bacterial cells and/or endospores to produce a first signal;
   after labeling the sample with the nucleic acid intercalating agent to produce the first signal, detecting the first signal from the sample;
   treating the sample by heating the sample to a temperature for a suitable duration or by exposing the sample to ultraviolet (UV) radiation or by contacting the sample to one or more chemicals to render accessible nucleic acids from the viable bacterial cell and/or endospore;
   after the treating, labeling the sample with the nucleic acid intercalating agent to produce a second signal, the second signal produced upon labeling of the nucleic acids rendered accessible from the viable bacterial cell and/or endospore;
   after labeling the sample with the nucleic acid intercalating agent to produce the second signal, detecting the second signal from the sample; and
   subtracting the first signal from the second signal to detect the viable bacteria cells and/or endospore in the sample.

* * * * *

```
                        SEQUENCE LISTING

<160> NUMBER OF SEQ ID NOS: 4

<210> SEQ ID NO 1
<211> LENGTH: 18
<212> TYPE: DNA
<213> ORGANISM: artificial sequence
<220> FEATURE:
<223> OTHER INFORMATION: Synthetic polynucleotide

<400> SEQUENCE: 1
cggtgaatac gttcycgg                                              18

<210> SEQ ID NO 2
<211> LENGTH: 19
<212> TYPE: DNA
<213> ORGANISM: artificial sequence
<220> FEATURE:
<223> OTHER INFORMATION: Synthetic polynucleotide

<400> SEQUENCE: 2
ggwtaccttg ttacgactt                                             19

<210> SEQ ID NO 3
<211> LENGTH: 20
<212> TYPE: DNA
<213> ORGANISM: artificial sequence
<220> FEATURE:
<223> OTHER INFORMATION: Synthetic polynucleotide

<400> SEQUENCE: 3
tgaagatgtg cgagaaggct                                            20

<210> SEQ ID NO 4
<211> LENGTH: 20
<212> TYPE: DNA
<213> ORGANISM: artificial sequence
<220> FEATURE:
<223> OTHER INFORMATION: Synthetic polynucleotide

<400> SEQUENCE: 4
aggatcttcc ctcttaacgg                                            20
```